(12) United States Patent
Senoo et al.

(10) Patent No.: US 8,273,932 B2
(45) Date of Patent: Sep. 25, 2012

(54) PROCESS FOR PRODUCING ALKYLATED AROMATIC COMPOUNDS AND PROCESS FOR PRODUCING PHENOL

(75) Inventors: Shinji Senoo, Takaishi (JP); Kazuhiko Kato, Yokohama (JP); Kenji Doi, Ichihara (JP); Katsunari Higashi, Ichihara (JP)

(73) Assignee: Mitsui Chemicals, Inc., Tokyo (JP)

( * ) Notice: Subject to any disclaimer, the term of this patent is extended or adjusted under 35 U.S.C. 154(b) by 119 days.

(21) Appl. No.: 12/997,433

(22) PCT Filed: Jun. 3, 2009

(86) PCT No.: PCT/JP2009/060132
§ 371 (c)(1),
(2), (4) Date: Dec. 10, 2010

(87) PCT Pub. No.: WO2009/150973
PCT Pub. Date: Dec. 17, 2009

(65) Prior Publication Data
US 2011/0092745 A1    Apr. 21, 2011

(30) Foreign Application Priority Data

Jun. 10, 2008   (JP) .................................. 2008-151479

(51) Int. Cl.
*C07C 1/20* (2006.01)
*C07C 33/18* (2006.01)
*C07C 33/34* (2006.01)
*C07C 39/00* (2006.01)

(52) U.S. Cl. ......................... 585/469; 568/715; 568/716

(58) Field of Classification Search .................. 585/469; 568/715, 716
See application file for complete search history.

(56) References Cited

U.S. PATENT DOCUMENTS

| | | | |
|---|---|---|---|
| 5,015,786 A | 5/1991 | Araki et al. | |
| 5,081,321 A | 1/1992 | Fukuhara et al. | |
| 6,372,927 B2 | 4/2002 | Tatsumi et al. | |
| 7,524,788 B2 | 4/2009 | Girotti et al. | |
| 2004/0162448 A1 | 8/2004 | Yang et al. | |

FOREIGN PATENT DOCUMENTS

| | | |
|---|---|---|
| JP | 57-91972 | 6/1982 |
| JP | 2-174737 | 7/1990 |
| JP | 02-231442 | 9/1990 |
| JP | 2724001 | 11/1997 |
| JP | 11-35497 | 2/1999 |
| JP | 11-116523 | 4/1999 |
| JP | 11-347574 | 12/1999 |
| JP | 2003-523985 | 8/2003 |
| JP | 2005-513116 | 4/2005 |
| JP | 2005-314424 | 11/2005 |
| WO | 96-04225 | 2/1996 |
| WO | 03053892 | 7/2003 |

OTHER PUBLICATIONS

International Search Report dated Aug. 31, 2009.
Ipatieff, V., Teodorovitch, V.P., Levine, I.M., Solubility of Hydrogen and Natural Gas in Oil at High Operating Temperature and Pressure., The Oil and Gas Journal, 32, pp. 14, 30, and 31, Oct. 5, 1933.
Extended European Search Report dated Jun. 20, 2011.
Barman S. et al. "Kinetics of Reductive Isopropylation of Benzene with Acetone over Nano-Copper Chromite-Loaded H-Mordenite"; Industrial & Engineering Chemistry Research, American Chemical Society, US, vol. 45, No. 10; Apr. 14, 2006; pp. 3481-3487, XP002552820.
Sokolov V., J. Appl. Chem. USSR, 50(6), 1347-1349, (1977).
Thompson W. H., J. Chem. Eng. Data, 9(4), 516-520, (1964).
Englin B. A., Khim. Tekhnol. Topl. Masel, 10(9), 42-46, (1965).

*Primary Examiner* — Thuan D Dang
(74) *Attorney, Agent, or Firm* — Rankin, Hill & Clark LLP

(57) ABSTRACT

The process for producing alkylated aromatic compounds includes feeding raw materials including an aromatic compound, a ketone and hydrogen in a gas-liquid downward concurrent flow mode to a fixed-bed reactor packed with a catalyst thereby to produce an alkylated aromatic compound, wherein the catalyst includes a solid acid component and a metal component, the catalyst is loaded in the fixed-bed reactor such that the catalyst forms a catalyst layer, and the reaction gas flow rate defined by Equation (1) below is not less than 0.05 at an entrance of a layer containing the solid acid:

$$\rho g \cdot ug \cdot [\rho air \cdot \rho water/(\rho g \cdot \rho l)]^{1/2} \ (kgm^{-2}s^{-1}).$$

20 Claims, 1 Drawing Sheet

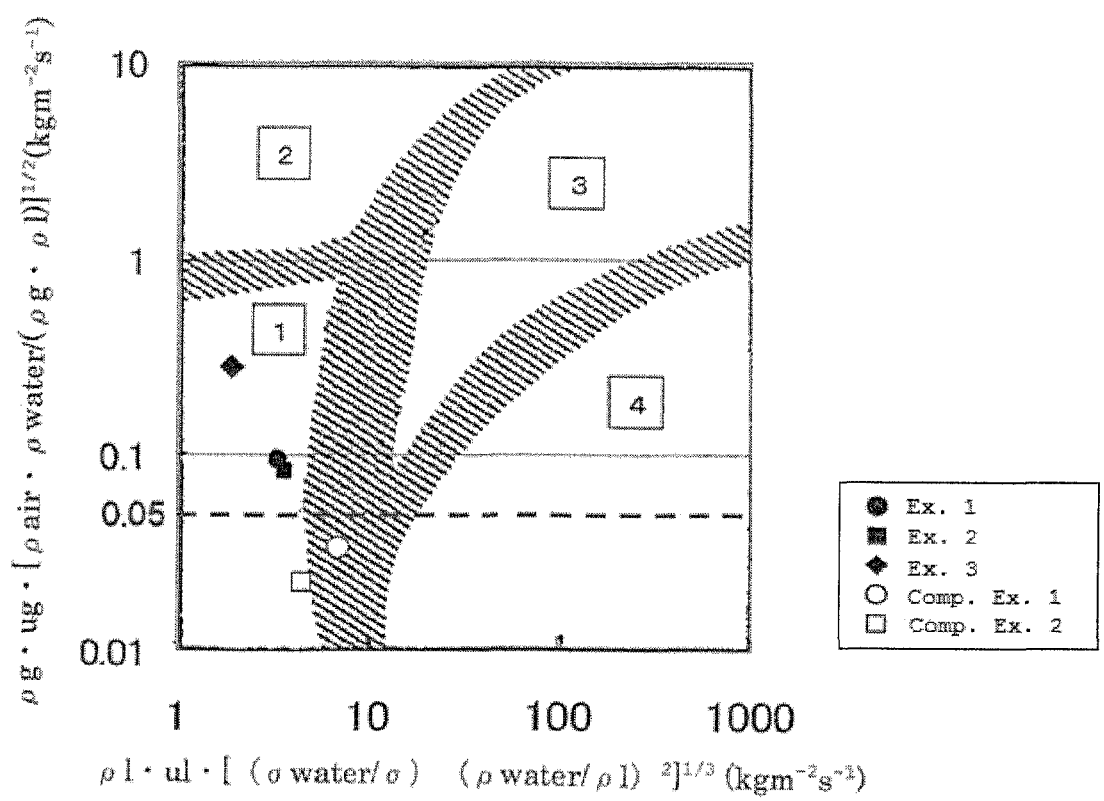

PROCESS FOR PRODUCING ALKYLATED AROMATIC COMPOUNDS AND PROCESS FOR PRODUCING PHENOL

FIELD OF INVENTION

The present invention relates to processes for producing alkylated aromatic compounds and processes for producing phenol.

BACKGROUND ART

A reaction between benzene and propylene gives cumene. Oxidation of cumene results in cumene hydroperoxide. The cumene hydroperoxide is acid decomposed into phenol and acetone. A combination of these known reactions is the cumene process which is currently a mainstream process for the production of phenol.

The cumene process gives acetone as a by-product, and is therefore valuable when both phenol and acetone are required. However, if the acetone produced is in excess of demand, the economic efficiency is deteriorated due to the price difference between acetone and starting material propylene. Methods have been then proposed which are aimed at benefitting from the price difference between starting material olefins and by-product ketones. For example, secondary butyl benzene obtained from n-butene and benzene is oxidized and acid decomposed to give phenol and methyl ethyl ketone (Patent Literatures 1 and 2). According to this method, the oxidation of the secondary butyl benzene achieves only about 80% selectivity for the target secondary butyl benzene hydroperoxide, with 15% or more by-product acetophenone. This method consequently provides a lower yield of phenol than by the cumene process.

It is also proposed that cyclohexyl benzene obtained from cyclohexene and benzene is oxidized and acid decomposed into phenol and cyclohexanone. Since the cyclohexanone obtained is dehydrogenated into phenol, this method does not technically involve the by-production of ketones. However, the method has a low industrial value because the oxidation of the cyclohexyl benzene provides a low yield of the target cyclohexyl benzene hydroperoxide.

The highest yields in oxidation and acid decomposition are achieved by the cumene process as described above. The problem related to starting material propylene and by-product acetone should be avoided while maintaining the advantageous yields. Methods have been then proposed in which the by-product acetone is treated by various methods and is reused as a material in the cumene process.

Acetone is readily hydrogenated to isopropanol, and the isopropanol is dehydrated to propylene. Patent Literature 3 discloses a process in which acetone is reused as a material in the cumene process, in detail cumene is produced by reacting benzene and propylene obtained from acetone as described above. However, the hydrogenation and the dehydration add two steps.

Patent Literatures 4 to 6 disclose methods in which isopropanol from the hydrogenation of acetone is directly reacted with benzene to give cumene. In particular, Patent Literature 6 discloses a process in which by-product acetone is hydrogenated to isopropanol, the isopropanol is reacted with benzene, and the resultant cumene is reacted to give phenol. In this process, however, the hydrogenation adds a step to the cumene process.

Patent Literature 7 describes a method in which by-product acetone is reused without adding a step to the conventional cumene process. In detail, ketone, e.g., acetone is reacted directly with aromatic compound, e.g., benzene and hydrogen in the presence of a catalyst composition including a solid acid substance and copper to give an alkylated aromatic compound.

However, Patent Literature 7 does not disclose that the reaction is performed in a trickle-bed zone.

Citation List

Patent Literature

Patent Literature 1: JP-A-S57-91972
Patent Literature 2: U.S. Patent Publication 2004/0162448
Patent Literature 3: JP-A-H02-174737
Patent Literature 4: JP-A-H02-231442
Patent Literature 5: JP-A-H11-35497
Patent Literature 6: JP-A-2003-523985
Patent Literature 7: JP-A-2005-513116

SUMMARY OF INVENTION

Technical Problem

When acetone is used as the alkylating agent in the cumene production, water that is by-produced during the reaction covers the acid sites of a zeolite catalyst to weaken the acid strength. It is therefore expected that the catalytic activity and the catalyst life are lowered compared to conventional processes using propylene as the alkylating agent. Accordingly, larger amounts of catalysts are required and the reactor size should be excessively large, increasing equipment costs.

Such disadvantages should be solved in the industrial cumene production by alkylating benzene with acetone.

It is an object of the present invention to provide an efficient process for producing alkylated aromatic compounds such as cumene by directly reacting an aromatic compound such as benzene with a ketone such as acetone and hydrogen in a compact reactor. It is another object of the invention to provide a process for producing phenol which includes a step of producing cumene by the above alkylation process.

Solution to Problem

The present inventors studied diligently to solve the aforementioned problems. They have then found that alkylated aromatic compounds may be obtained with very high ketone conversion and very high selectivity for alkylated aromatic compounds by feeding raw materials including an aromatic compound, a ketone and hydrogen in a gas-liquid downward concurrent flow mode to a fixed-bed reactor packed with a catalyst, and reacting the raw materials while regulating the components constituting the catalyst and the reaction gas flow rate.

The present invention is concerned with processes for producing alkylated aromatic compounds and processes for producing phenol as described in (1) to (9) below.

(1) A process for producing alkylated aromatic compounds comprising feeding raw materials including an aromatic compound, a ketone and hydrogen in a gas-liquid downward concurrent flow mode to a fixed-bed reactor packed with a catalyst thereby to produce an alkylated aromatic compound, wherein
the catalyst comprises a solid acid component and a metal component comprising at least one metal selected from the group consisting of copper, nickel, cobalt and rhenium, the catalyst is loaded in the fixed-bed reactor such that the catalyst forms a catalyst layer having a single layer or a plurality of layers, and the reaction gas flow rate defined by Equation (1) below is not less than 0.05 at an entrance of a layer containing the solid acid which layer is included in the catalyst layer:

$$\rho g \cdot ug \cdot [\rho air \cdot \rho water/(\rho g \cdot \rho l)]^{1/2} \; (kgm^{-2}s^{-1}) \quad (1)$$

wherein $\rho g$ is the density of the reaction gas, $\rho l$ is the density of the reaction liquid, $\rho air$ is the gas density of air, $\rho water$ is the gas density of water, and ug is the superficial velocity of the reaction gas.

(2) The process for producing alkylated aromatic compounds as described in (1), wherein the catalyst layer is a single catalyst layer (A) comprising the catalyst or is a catalyst layer (B) which includes an upstream layer 1 comprising the metal component and a downstream layer 2 comprising the solid acid component or comprising the solid acid component and the metal component, and wherein the entrance of a layer containing the solid acid is an entrance of the catalyst layer (A) or an entrance of the layer 2.

(3) The process for producing alkylated aromatic compounds as described in (1) or (2), wherein the flow state in the reactor is in a trickle-bed zone.

(4) The process for producing alkylated aromatic compounds as described in any one of (1) to (3), wherein the metal component further comprises at least one element selected from the group consisting of Group IIB elements, Group IIIA elements, Group VIB elements and Group VIII elements (except nickel and cobalt).

(5) The process for producing alkylated aromatic compounds as described in any one of (1) to (4), wherein the solid acid component is zeolite.

(6) The process for producing alkylated aromatic compounds as described in (5), wherein the zeolite has a ten to twelve-membered ring structure.

(7) The process for producing alkylated aromatic compounds as described in any one of (1) to (6), wherein the catalyst layer is a catalyst layer (B) which includes an upstream layer 1 comprising the metal component and a downstream layer 2 comprising the solid acid component or comprising the solid acid component and the metal component.

(8) The process for producing alkylated aromatic compounds as described in any one of (1) to (7), wherein the aromatic compound is benzene and the ketone is acetone.

(9) A process for producing phenol, comprising the step (a) to the step (d) described below wherein the step (c) is performed according to the process for producing alkylated aromatic compounds described in (8);

step (a): a step of oxidizing cumene into cumene hydroperoxide;

step (b): a step of acid decomposing the cumene hydroperoxide to obtain phenol and acetone;

step (c): a step of reacting the acetone from the step (b) with benzene and hydrogen to synthesize cumene; and step (d): a step of circulating the cumene from the step (c) to the step (a).

Advantageous Effects of Invention

According to the processes for producing alkylated aromatic compounds of the present invention, starting materials (raw materials) including a ketone such as acetone, an aromatic compound such as benzene and hydrogen are reacted together in a single reaction step to give an alkylaromatic compound such as cumene with higher yield than achieved heretofore. The processes of the invention thus provide industrial and practical advantages. The cumene produced according to the processes of the invention is of the same quality as cumene obtained from propylene or isopropanol and benzene.

The processes for producing phenol according to the invention have adopted the above process of producing alkylated aromatic compounds, and thereby acetone that is by-produced in the phenol production is recycled without increasing the number of steps of the conventional cumene process. The processes for producing phenol of the present invention can produce phenol with great process advantages and economic advantages.

BRIEF DESCRIPTION OF DRAWING

FIG. 1 is a plot diagram in which flow states in Examples and Comparative Examples are plotted in a diagram showing flow zones in gas-liquid downward concurrent packed layers that is described in "Shokubai Kouza (Catalyst Courses) Vol. 6, (Engineering Part 2), Shokubai Hannou Souchi to Sono Sekkei (Catalyst reaction apparatus and its design)", Catalysts Society of Japan, Kodansha Ltd., December 1985, first impression, p. 182.

DESCRIPTION OF EMBODIMENTS

In a process for producing alkylated aromatic compounds according to the present invention, raw materials including an aromatic compound, a ketone and hydrogen are fed in a gas-liquid downward concurrent flow mode to a fixed-bed reactor packed with a catalyst to produce an alkylated aromatic compound. The catalyst comprises a solid acid component and a metal component comprising at least one metal selected from the group consisting of copper, nickel, cobalt and rhenium. The catalyst is loaded in the fixed-bed reactor such that the catalyst forms a catalyst layer having a single layer or a plurality of layers. The reaction gas flow rate defined by Equation (1) below is not less than 0.05 at an entrance of a layer containing the solid acid which layer is included in the catalyst layer:

$$\rho g \cdot ug \cdot [\rho air \cdot \rho water/(\rho g \cdot \rho l)]^{1/2} \; (kgm^{-2}s^{-1}) \quad (1)$$

wherein $\rho g$ is the density of the reaction gas, $\rho l$ is the density of the reaction liquid, $\rho air$ is the gas density of air, $\rho water$ is the gas density of water, and ug is the superficial velocity of the reaction gas.

In the processes for producing alkylated aromatic compounds, the raw materials including an aromatic compound, a ketone and hydrogen are fed to a fixed-bed reactor packed with a catalyst, and the ketone is hydrogenated in the reactor to an alcohol and the alcohol alkylates the aromatic compound.

The reaction mode in the processes for producing alkylated aromatic compounds is in detail as follows. The metal component forming the catalyst catalyzes the hydrogenation of the ketone into an alcohol. The hydrogenation is preferably carried out by a gas liquid solid three phase reaction in a trickle-bed zone (perfusate flow) as described in the hydrogenation reaction in Japanese Patent No. 2724001. In the trickle-bed zone, the liquid trickles over the outer surface of the catalyst and part thereof is attached to narrow pores in the catalyst. In either case, the liquid is scattered as individual masses forming a dispersed phase. Meanwhile, the gas surrounds the catalyst and the liquid, forming a continuous phase. Flow zones in gas-liquid downward concurrent packed layers are shown in FIG. 1. FIG. 1 is based on data obtained with an air-water system. Flow zones with other systems in FIG. 1 may be prepared in consideration of correction terms based on differing physical properties. The shaded parts indicate ranges where boundaries exist ("Shokubai Kouza (Catalyst Courses) Vol. 6, (Engineering Part 2), Shokubai Hannou Souchi to Sono Sekkei (Catalyst reaction apparatus and its design)", Catalysts Society of Japan, Kodansha Ltd., December 1985, first impression, p. 182). The trickle-bed zone has the same definition as the perfusate flow zone.

When the reactants in the reactor have a flow state in the trickle-bed zone, the concentration distribution in the system is uniform and mild operation is possible, the facility does not have to be high-pressure resistant, the physical load on the catalyst is lowered, and catalyst damage is prevented as described in JP-A-H11-116523.

After the alcohol formation by the hydrogenation of ketone, the solid acid component forming the catalyst catalyzes the alkylation of the aromatic compound with the alcohol to afford an alkylated aromatic compound. This reaction is a liquid solid two phase reaction. In the system, however, hydrogen which has been fed in excess for the hydrogenation reaction is present although such hydrogen is not involved in the alkylation reaction. Accordingly, the system has three, namely gas, liquid and solid, phases. According to the invention, hydrogen which is not involved in the alkylation reaction is supplied in an increased amount and thereby the results of alkylation reaction by the alcohol are drastically improved. In view of stable operation of the reactor and reduced catalyst damages, the alkylation of the aromatic compound with the alcohol is preferably performed in a trickle-bed zone (perfusate flow).

That is, the flow state in the reactor in the processes for producing alkylated aromatic compounds of the invention is preferably in a trickle-bed zone.

As described above, the process for producing alkylated aromatic compounds of the invention involves two reactions: hydrogenation and alkylation, and the metal component catalyzes the hydrogenation and the solid acid component contributes to the alkylation. The catalyst used in the invention is formed of the solid acid component and the metal component including at least one metal selected from the group consisting of copper, nickel, cobalt and rhenium. The catalyst may be loaded in a fixed-bed reactor in any manner without limitation as long as the catalyst forms a catalyst layer having a single layer or a plurality of layers.

Examples of the catalyst layers include a single catalyst layer (A) formed of the catalyst, a catalyst layer (B) which has an upstream layer 1 formed of the metal component and a downstream layer 2 formed of the solid acid component or formed of the solid acid component and the metal component, and a catalyst layer (3) in which a layer formed of the metal component and a layer formed of the solid acid component are alternately stacked. In particular, from the viewpoints of economic efficiency and catalyst loading rationality in the setting up of the reactor which are attributed to the simple constitution of the catalyst layer, the catalyst layer is preferably a single catalyst layer (A) formed of the catalyst or a catalyst layer (B) which has an upstream layer 1 formed of the metal component and a downstream layer 2 formed of the solid acid component or formed of the solid acid component and the metal component.

In a particularly preferred embodiment, the catalyst is loaded in a fixed-bed reactor to constitute the catalyst layer (B). According to this preferred embodiment, the raw materials are first passed through the layer 1 which is formed of the metal component catalyzing the hydrogenation and are thereafter passed through the layer 2 which contains the solid acid component catalyzing the alkylation, and thereby alkylated aromatic compounds may be obtained efficiently.

In the invention, the reaction gas flow rate defined by Equation (1) below is not less than 0.05 at an entrance of a layer containing the solid acid which layer is included in the catalyst layer. In the case where the catalyst layer is the catalyst layer (A), the catalyst layer (A) itself is the layer containing the solid acid. When the catalyst layer is the catalyst layer (B), the layer 2 is the layer containing the solid acid. In the invention, the reaction gas refers to a gas phase component in the reactor. That is, the reaction gas includes all components existing in the form of gas, in detail hydrogen fed as a raw material, evaporated aromatic compound and ketone, and evaporated alkylated aromatic compound, water and alcohol. In the invention, the reaction liquid refers to a liquid phase component in the reactor. That is, the reaction liquid includes all components existing in the form of liquid, in detail aromatic compound and ketone fed as raw materials, hydrogen dissolved in the liquid phase, and alkylated aromatic compound, water and alcohol.

$$\rho g \cdot ug \cdot [\rho air \cdot \rho water/(\rho g \cdot \rho l)]^{1/2} \, (kgm^{-2}s^{-}) \quad (1)$$

wherein $\rho g$ is the density of the reaction gas, $\rho l$ is the density of the reaction liquid, $\rho air$ is the gas density of air, $\rho water$ is the gas density of water, and $ug$ is the superficial velocity of the reaction gas.

Equation (1) above corresponds to the y-axis in the flow zone diagram in FIG. 1. When the reaction gas flow rate defined by Equation (1) is 0.05 or above, high cumene selectivity is achieved. The reaction gas flow rate is more preferably in the range of 0.08 to 0.6.

In FIG. 1, the x-axis indicates the flow rate of the reaction liquid, represented by Equation (2) below. The reaction liquid flow rate represented by Equation (2) has been found less influential to the efficiency and results of the production of alkylated aromatic compounds by the processes according to the present invention, compared to the reaction gas flow rate expressed by Equation (1).

$$\rho l \cdot ul \cdot [(\sigma water/\sigma)(\rho water/\rho l)^2]^{1/3} \, (kgm^{-2}s^{-1}) \quad (2)$$

wherein $\rho l$ is the density of the reaction liquid, $\rho water$ is the gas density of water, $\sigma$ is the surface tension of the reaction liquid, $\sigma water$ is the surface tension of water, and $ul$ is the superficial velocity of the reaction liquid.

As described hereinabove, it is preferable in the processes for producing alkylated aromatic compounds that the flow state in the reactor is in a trickle-bed zone. The flow rate of the reaction liquid does not adversely affect the processes of the invention as long as the flow state is in a trickle-bed zone.

Examples of the aromatic compounds used in the processes for producing alkylated aromatic compounds include benzene and naphthalene, with benzene being preferred. Examples of the ketones include acetone and methyl ethyl ketone, with acetone being preferred.

That is, in a preferred embodiment of the processes for producing alkylated aromatic compounds of the invention, the aromatic compound is benzene and the ketone is acetone, and the alkylated aromatic compound obtained in this case is cumene.

The catalyst used in the invention includes a solid acid component and a metal component containing at least one metal selected from the group consisting of copper, nickel, cobalt and rhenium. The catalyst may include other components. The catalyst may be formed (prepared) by any methods without limitation. In an embodiment, the solid acid component and the metal component containing at least one metal selected from copper, nickel, cobalt and rhenium may be physically mixed on a catalyst particle level with a centimeter size. In another embodiment, the solid acid component and the metal component containing at least one metal selected from copper, nickel, cobalt and rhenium may be separately pulverized to a finely small size and mixed together, and the mixture may be shaped into catalyst particles with a centimeter size. In a still another embodiment, the solid acid component may be used as a carrier, and the metal component containing at least one metal selected from copper, nickel, cobalt and rhenium may be supported thereon. Alternatively, the metal component containing at least one metal selected from copper, nickel, cobalt and rhenium may be used as a carrier, and the solid acid component may be supported thereon.

The solid acid components used in the invention are catalysts that function as acids. Examples of the solid acid components include usual solid acids such as zeolite, silica alumina, alumina, sulfate-promoted zirconia and $WO_3$-promoted zirconia.

In particular, the zeolites that are inorganic crystalline porous compounds composed of silicon and aluminum are suitable solid acid components from the viewpoints of heat resistance and selectivity for the target alkylated aromatic compounds (such as cumene).

For the production of cumene as the alkylated aromatic compound, a zeolite is preferably used which has a ten to twelve-membered ring structure having a pore similar in size to the molecular diameter of cumene.

Examples of the zeolites having a twelve-membered ring structure include Y-type zeolite, USY-type zeolite, mordenite type zeolite, dealuminated mordenite type zeolite, β-zeolite, MCM-22-type zeolite and MCM-56-type zeolite. In particular, β-zeolite, MCM-22-type zeolite and MCM-56-type zeolite have suitable structures.

In the zeolites, the composition ratio between silicon and aluminum may be suitably in the range of 2/1 to 200/1, and in view of activity and heat stability, preferably in the range of 5/1 to 100/1. Further, isomorphously substituted zeolites may be used in which aluminum atoms in the zeolite skeleton are substituted with other metal such as Ga, Ti, Fe, Mn or B.

The shape of the solid acid components is not particularly limited, and the solid acid components may be in the form of sphere, cylindrical column, extrudate or crushed pieces. The size of the particles of the solid acid components may be selected in the range of 0.01 mm to 100 mm depending on the size of a reactor.

The metal components containing at least one metal selected from copper, nickel, cobalt and rhenium may be metal simple substances, metal oxides such as $ReO_2$, $Re_2O_7$, NiO and CuO, metal chlorides such as $ReCl_3$, $NiCl_2$ and $CuCl_2$, and cluster metals such as Ni—Cu and Ni—Cu—Cr.

The metal components containing at least one metal selected from copper, nickel, cobalt and rhenium are not particularly limited as long as they have a capability of hydrogenating the carbonyl functional groups into alcohols. Commercially available hydrogenation catalysts may be used. For example, such catalysts are marketed as supported catalysts on various carriers, with examples including 5% Re carbon catalysts, 5% Re alumina catalysts, silica alumina-supported nickel catalysts and catalysts supported on these carriers in varied amounts, for example 1% or 0.5%. In a preferred embodiment, at least one carrier is selected from silica, alumina, silica alumina, titania, magnesia, silica magnesia, zirconia and carbon.

The shape of the metal components containing at least one metal selected from copper, nickel, cobalt and rhenium is not particularly limited, and they may be in the form of sphere, cylindrical column, extrudate or crushed pieces. The size of the particles of the metal components may be selected in the range of 0.01 mm to 100 mm depending on the size of a reactor.

The metal components containing at least one metal selected from copper, nickel, cobalt and rhenium may further contain at least one element selected from the group consisting of Group IIB elements, Group IIIA elements, Group VIB elements and Group VIII elements (except nickel and cobalt).

Specific examples of such elements include Zn, Cd, Hg, B, Al, Ga, In, Tl, Cr, Mo, W, Fe, Ru, Os, Rh, Ir, Pd and Pt.

From the viewpoint of extended catalyst life, it is preferable that the metal component contain Zn or Al in addition to cupper.

The catalysts of the invention may increase activity or selectivity by containing metal salts such as $PbSO_4$, $FeCl_2$ and $SnCl_2$, alkali metals and alkali metal salts such as K and Na, and $BaSO_4$. Such components may be added to the catalysts as required.

In an embodiment, the metal component containing at least one metal selected from copper, nickel, cobalt and rhenium may be supported on the solid acid component as a carrier. In detail, such supported catalysts may be prepared by impregnating the solid acid component with an aqueous solution of the metal nitrate and calcining the impregnated catalyst. Alternatively, the metal may be bonded with an organic molecule ligand to become soluble in organic solvents, and the solid acid component may be impregnated with a solution of the metal-ligand complex in an organic solvent and thereafter calcined. Taking advantage of the characteristic that some of the complexes are vaporized under vacuum, such complexes may be supported on the solid acid component by deposition or the like. Further, a coprecipitation method may be adopted in which the solid acid component is obtained from a corresponding metal salt in the presence of a metal salt which will form the hydrogenation catalyst and thereby the synthesis of the solid acid component and the supporting of the metal are carried out simultaneously.

To achieve high productivity, the supply rate for the raw materials in the invention, in detail the liquid weight hourly space velocity (WHSV) relative to the catalyst weight is preferably in the range of 0.1 to 200/h, and more preferably 0.2 to 100/h. Herein, the liquid weight refers to the total weight of the aromatic compound and the ketone.

In the invention, the process for producing alkylated aromatic compounds is carried out in the presence of hydrogen. Theoretically, hydrogen may be used at least in an equimolar amount relative to the ketone. From the viewpoints of separation and recovery, the hydrogen may be preferably used in an equimolar to twenty-fold molar amount, and more preferably in an equimolar to ten-fold molar amount relative to the ketone. When the ketone conversion is desired to be less than 100%, the hydrogen amount may be controlled less than the equimolar amount. In the reaction of the invention, the hydrogen reacts with the oxygen atom in the ketone to form water, and the water produced is discharged from a reactor outlet together with the alkylated aromatic compound. Accordingly, an excess of hydrogen over the ketone is not substantially consumed as long as undesirable side reactions take place.

Theoretically, the aromatic compound may be used at least in an equimolar amount relative to the ketone. From the viewpoints of separation and recovery, the aromatic compound may be preferably used in an equimolar to ten-fold molar amount, and more preferably in an equimolar to five-fold molar amount relative to the ketone.

In the processes for producing alkylated aromatic compounds, the raw materials are fed to a fixed bed reactor in a gas-liquid downward concurrent flow mode. The reaction temperature in the reactor is in the range of 100 to 300° C., and preferably 120 to 250° C. The reaction pressure is in the range of 0.5 to 10 MPaG, and preferably 2 to 5 MPaG.

A process for producing phenol according to the present invention includes the step (a) to the step (d) described below wherein the step (c) is performed according to the process for producing alkylated aromatic compounds described hereinabove. In the process for producing alkylated aromatic compounds which is performed as the step (c) in the phenol production process, the aromatic compound is benzene and the ketone is acetone.

Step (a): a step of oxidizing cumene into cumene hydroperoxide;

Step (b): a step of acid decomposing the cumene hydroperoxide to obtain phenol and acetone;

Step (c): a step of reacting the acetone from the step (b) with benzene and hydrogen to synthesize cumene; and Step (d): a step of circulating the cumene from the step (c) to the step (a).

In the process for producing phenol, phenol is formed from cumene in the steps (a) and (b), the by-product acetone is reacted in the step (c) to form cumene, and the cumene formed in the step (c) is recycled in the step (e) back to the step (a). Accordingly, it is theoretically not necessary that acetone should be fed from the outside of the reaction system, achieving cost advantages. In practical plants, it is difficult to recover 100% acetone and therefore at least an amount of acetone corresponding to the decrease is newly fed to the reaction system.

Various modifications and improvements may be made to the processes for producing phenol according to the invention.

EXAMPLES

The present invention will be described by presenting examples but the invention is not limited to such examples as long as within the scope of the invention.

Example 1

A catalyst test was carried out in which cumene was produced from raw materials: acetone, benzene and hydrogen.

Cu—Zn catalyst (cylindrical columns 3 mm in diameter×3 mm in height, manufactured by Süd-Chemie Catalysts Japan, Inc., elemental mass %: Cu 32 to 35%, Zn 35 to 40%, Al 6 to 7%, Zn to Cu atomic ratio: 1.0 to 1.2) weighing 1496 g was loaded at an upper part of a stainless steel vertical reaction tube 38.4 mm in inner diameter (having an 8 mm inner tube) and 4800 mm in length. β-zeolite catalyst (pellets 1.5 mm in diameter, manufactured by TOSOH CORPORATION) weighing 1806 g was loaded at a lower part of the reactor. A catalyst layer was thereby formed which had a layer 1 of the Cu—Zn catalyst and a layer 2 of the β-zeolite catalyst.

After the loading, isopropanol was supplied from the top of the reactor at 24 L/h and the catalyst was washed for 1 hour. After the completion of the washing, the catalyst was activated by passing hydrogen at 630 NL/h, at 3 MPaG and a preheating temperature of 100° C. for 3 hours.

While the reactor pressure was maintained at 3 MPaG and the preheating temperature at 170° C., benzene: 7.0 L/h, acetone: 0.59 L/h and hydrogen: 830 NL/h were supplied from the top of the reactor to perform reaction. A mixture of the reaction liquid and gas that was discharged from the reactor bottom was separated in a gas-liquid separation tank, and the oil phase and the aqueous phase were separated in an oil-water separation tank. When the reaction had been continuously carried out for 12 hours, the reaction liquid and the waste gas were each analyzed by gas chromatography. The gas chromatography showed that the acetone conversion was 94.5% and the cumene selectivity was high at 96.9%.

Separately, a flow zone under the above conditions was studied. The reaction gas flow rate at the entrance of the layer 2 (the alkylation catalyst layer) was calculated using the PSRK equation (Kagaku Kougaku Binran (Chemical Engineering Handbook), revised 6th edition, edited by The Society for Chemical Engineers, Japan.) as an estimation equation which had been corrected by regressing literature data including solubility data of hydrogen in benzene and cumene (Ipatieff V., Oil Gas J. 32, 14-15, (1993) and Sokolov V., J. Appl. Chem. USSR, 50(6), 1347-1349, (1977)), solubility data of benzene and cumene in water (Thompson W. H., J. Chem. Eng. Data, 9(4), 516-520, (1964) and Englin B. A., Khim. Tekhnol. Topl. Masel, 10(9), 42-46, (1965)) and benzene/water azeotropic data (Burd S. D., Proc. Am. Petrol. Inst. Ref. Div., 48, 464-476, (1968)).

Properties were estimated by inputting the above estimation equation and reaction conditions in Examples in a stationary process simulator (manufactured by Aspen Tech Japan Co., Ltd.). The results are set forth in Table 1.

In Example 1, the flow state was in a trickle-bed zone and the reaction gas flow rate at the layer 2 was 0.095.

x-axis (Equation (2)): $\rho l \cdot ul \cdot [(\sigma water/\sigma)(\rho water/\rho l)^2]^{1/3}$ $(kgm^{-2}s^{-1})$=3.430 y-axis (Equation (1)): $\rho g \cdot ug \cdot [\rho air \cdot \rho water/(\rho g \cdot \rho l)]^{1/2}$ $(kgm^{-2}s^{-1})$=0.095

Example 2

A catalyst test was carried out with the same experimental apparatus and under the same reaction conditions as in Example 1, except that the reactor pressure was changed to 4 MPaG and the preheating temperature was 185° C. The acetone conversion was 97.0% and the cumene selectivity was high at 92.9%. The results are set forth in Table 1.

In Example 2, the flow state was in a trickle-bed zone and the reaction gas flow rate at the layer 2 was 0.083.

x-axis (Equation (2)): $\rho l \cdot ul \cdot [(\sigma water/\sigma)(\rho water/\rho l)^2]^{1/3}$ $(kgm^{-2}s^{-1})$=3.746 y-axis (Equation (1)): $\rho g \cdot ug \cdot [\rho air \cdot \rho water/(\rho g \cdot \rho l)]^{1/2}$ $(kgm^{-2}s^{-1})$=0.083

Example 3

Cu—Zn catalyst (cylindrical columns 3 mm in diameter×3 mm in height, manufactured by Süd-Chemie Catalysts Japan, Inc., elemental mass %: Cu 32 to 35%, Zn 35 to 40%, Al 6 to 7%, Zn to Cu atomic ratio: 1.0 to 1.2) weighing 885 g was loaded in the reactor described in Example 1. β-zeolite catalyst (pellets 1.5 mm in diameter; manufactured by TOSOH CORPORATION) weighing 1806 g was loaded at a lower part of the reactor. A catalyst layer was thereby formed which had a layer 1 of the Cu—Zn catalyst and a layer 2 of the β-zeolite catalyst. The catalyst was washed and pretreated in the same manner as in Example 1.

While the reactor pressure was maintained at 3 MPaG and the preheating temperature at 173° C., benzene: 7.65 L/h, acetone: 0.59 L/h and hydrogen: 2090 NL/h were supplied from the top of the reactor to perform reaction. A mixture of the reaction liquid and gas that was discharged from the reactor bottom was separated in a gas-liquid separation tank, and the oil phase and the aqueous phase were separated in an oil-water separation tank. When the reaction had been continuously carried out for 12 hours, the reaction liquid and the waste gas were each analyzed by gas chromatography. The acetone conversion was 98.5% and the cumene selectivity was high at 98.9%. The results are set forth in Table 1.

In Example 3, the flow state was in a trickle-bed zone and the reaction gas flow rate at the layer 2 was 0.285.

x-axis (Equation (2)): $\rho l \cdot ul \cdot [(\sigma water/\sigma)(\rho water/\rho l)^2]^{1/3}$ $(kgm^{-2}s^{-1})$=1.949 y-axis (Equation (1)): $\rho g \cdot ug \cdot [\rho air \cdot \rho water/(\rho g \cdot \rho l)]^{1/2}$ $(kgm^{-2}s^{-1})$=0.285

Comparative Example 1

A catalyst test was carried out with the same experimental apparatus and under the same reaction conditions as in Example 2, except that the hydrogen was fed at 530 NL/h. The acetone conversion was 96.1% and the cumene selectivity was low at 87.9%. The results are set forth in Table 1.

In Comparative Example 1, the flow state was in a boundary zone between a trickle-bed zone (perfusate flow) and a bubble flow zone, and the reaction gas flow rate at the layer 2 was 0.033.

x-axis (Equation (2)): $\rho l \cdot ul \cdot [(\sigma water/\sigma)\,(\rho water/\rho l)^2]^{1/3}$ $(kgm^{-2}s^{-1})$=7.063 y-axis (Equation (1)): $\rho g \cdot ug \cdot [\rho air \cdot \rho water/(\rho g \cdot \rho l)]^{1/2}$ $(kgm^{-2}s^{-2})$=0.033.

Comparative Example 2

A catalyst test was carried out with the same experimental apparatus and under the same reaction conditions as in Example 3, except that the hydrogen was fed at 348 NL/h. The acetone conversion was 97.7% and the cumene selectivity was low at 35.7%. The results are set forth in Table 1.

In Comparative Example 2, the flow state was in a boundary zone between a trickle-bed zone (perfusate flow) and a bubble flow zone, and the reaction gas flow rate at the layer 2 was 0.022.

x-axis (Equation (2)): $\rho l \cdot ul \cdot [(\sigma water/\sigma)\,(\rho water/\rho l)^2]^{1/3}$ $(kgm^{-2}s^{-1})$=4.583 y-axis (Equation (1)): $\rho g \cdot ug \cdot [\rho air \cdot \rho water/(\rho g \cdot \rho l)]^{1/2}$ $(kgm^{-2}s^{-1})$=0.022

The invention claimed is:

1. A process for producing alkylated aromatic compounds comprising feeding raw materials including an aromatic compound, a ketone and hydrogen in a gas-liquid downward concurrent flow mode to a fixed-bed reactor packed with a catalyst thereby to produce an alkylated aromatic compound, wherein the catalyst comprises a solid acid component and a metal component comprising at least one metal selected from the group consisting of copper, nickel, cobalt and rhenium, the catalyst is loaded in the fixed-bed reactor such that the catalyst forms a catalyst layer having a single layer or a plurality of layers, and the reaction gas flow rate defined by Equation (1) below is not less than 0.05 at an entrance of a layer containing the solid acid which layer is included in the catalyst layer:

$$\rho g \cdot ug \cdot [\rho air \cdot \rho water/(\rho g \cdot \rho l)]^{1/2} \; (kgm^{-2}s^{-1}) \quad (1)$$

wherein $\rho g$ is the density of the reaction gas, $\rho l$ is the density of the reaction liquid, $\rho air$ is the gas density of air, $\rho water$ is the gas density of water, and ug is the superficial velocity of the reaction gas.

2. The process for producing alkylated aromatic compounds according to claim 1, wherein the catalyst layer is a single catalyst layer (A) comprising the catalyst or is a catalyst layer (B) which includes an upstream layer 1 comprising the metal component and a downstream layer 2 comprising the solid acid component or comprising the solid acid component and the metal component, and wherein the entrance of a layer containing the solid acid is an entrance of the catalyst layer (A) or an entrance of the layer 2.

3. The process for producing alkylated aromatic compounds according to claim 1, wherein the flow state in the reactor is in a trickle-bed zone.

4. The process for producing alkylated aromatic compounds according to claim 1, wherein the metal component further comprises at least one element selected from the

TABLE 1

| Properties at entrance of zeolite layer | | Ex. 1 | | Ex. 2 | | Comp. Ex. 1 | | Ex. 3 | | Comp. Ex. 2 | |
|---|---|---|---|---|---|---|---|---|---|---|---|
| | | Liquid phase component | Gas phase component | Liquid phase component | Gas phase component | Liquid phase component | Gas phase component | Liquid phase component | Gas phase component | Liquid phase component | Gas phase component |
| Surface tension | dyne/cm | 9.708 | — | 8.242 | — | 7.183 | — | 9.758 | — | 9.611 | — |
| Viscosity | cP | 0.142 | 0.017 | 0.128 | 0.017 | 0.118 | 0.017 | 0.142 | 0.017 | 0.141 | 0.016 |
| Density | kg/m$^3$ | 607.745 | 28.072 | 584.857 | 35.919 | 560.981 | 43.448 | 613.894 | 26.918 | 603.546 | 28.924 |
| Flow rate | kg/h | 5.253 | 1.485 | 5.295 | 1.445 | 9.273 | 0.626 | 3.009 | 4.401 | 6.962 | 0.357 |
| Superficial velocity | kg/m$^2 \cdot$s | 1.260 | 0.356 | 1.270 | 0.347 | 2.225 | 0.150 | 0.722 | 1.056 | 1.671 | 0.086 |
| x-axis (Eq. 2) | kg/m$^2 \cdot$s | 3.430 | | 3.746 | | 7.063 | | 1.949 | | 4.583 | |
| y-axis (Eq. 1) | kg/m$^2 \cdot$s | 0.095 | | 0.083 | | 0.033 | | 0.285 | | 0.022 | |

Reference Signs List 1 perfusate flow
2 mist flow
3 pulsating flow
4 bubble flow group consisting of Group IIB elements, Group IIIA elements, Group VIB elements and Group VIII elements (except nickel and cobalt).

5. The process for producing alkylated aromatic compounds according to claim 1, wherein the solid acid component is zeolite.

6. The process for producing alkylated aromatic compounds according to claim 5, wherein the zeolite has a ten to twelve-membered ring structure.

7. The process for producing alkylated aromatic compounds according to claim 1, wherein the catalyst layer is a catalyst layer (B) which includes an upstream layer 1 comprising the metal component and a downstream layer 2 comprising the solid acid component or comprising the solid acid component and the metal component.

8. The process for producing alkylated aromatic compounds according to claim 1, wherein the aromatic compound is benzene and the ketone is acetone.

9. A process for producing phenol, comprising the step (a) to the step (d) described below wherein the step (c) is performed according to the process for producing alkylated aromatic compounds described in claim 8;
step (a): a step of oxidizing cumene into cumene hydroperoxide;
step (b): a step of acid decomposing the cumene hydroperoxide to obtain phenol and acetone;
step (c): a step of reacting the acetone from the step (b) with benzene and hydrogen to synthesize cumene; and
step (d): a step of circulating the cumene from the step (c) to the step (a).

10. The process for producing alkylated aromatic compounds according to claim 2, wherein the flow state in the reactor is in a trickle-bed zone.

11. The process for producing alkylated aromatic compounds according to claim 2, wherein the metal component further comprises at least one element selected from the group consisting of Group IIB elements, Group IIIA elements, Group VIB elements and Group VIII elements (except nickel and cobalt).

12. The process for producing alkylated aromatic compounds according to claim 3, wherein the metal component further comprises at least one element selected from the group consisting of Group IIB elements, Group IIIA elements, Group VIB elements and Group VIII elements (except nickel and cobalt).

13. The process for producing alkylated aromatic compounds according to claim 2, wherein the solid acid component is zeolite.

14. The process for producing alkylated aromatic compounds according to claim 3, wherein the solid acid component is zeolite.

15. The process for producing alkylated aromatic compounds according to claim 4, wherein the solid acid component is zeolite.

16. The process for producing alkylated aromatic compounds according to claim 2, wherein the catalyst layer is a catalyst layer (B) which includes an upstream layer 1 comprising the metal component and a downstream layer 2 comprising the solid acid component or comprising the solid acid component and the metal component.

17. The process for producing alkylated aromatic compounds according to claim 3, wherein the catalyst layer is a catalyst layer (B) which includes an upstream layer 1 comprising the metal component and a downstream layer 2 comprising the solid acid component or comprising the solid acid component and the metal component.

18. The process for producing alkylated aromatic compounds according to claim 4, wherein the catalyst layer is a catalyst layer (B) which includes an upstream layer 1 comprising the metal component and a downstream layer 2 comprising the solid acid component or comprising the solid acid component and the metal component.

19. The process for producing alkylated aromatic compounds according to claim 2, wherein the aromatic compound is benzene and the ketone is acetone.

20. The process for producing alkylated aromatic compounds according to claim 3, wherein the aromatic compound is benzene and the ketone is acetone.

* * * * *